United States Patent

Hagemann et al.

Patent Number: 6,015,654
Date of Patent: Jan. 18, 2000

[54] COLOR PHOTOGRAPHIC RECORDING MATERIAL

[75] Inventors: Jörg Hagemann, Köln; Siegfried Dzwonnek, Pulheim, both of Germany

[73] Assignee: AGFA-Gevaert NV, Mortsel, Belgium

[21] Appl. No.: 09/020,610

[22] Filed: Feb. 9, 1998

[30] Foreign Application Priority Data

Feb. 18, 1997 [DE] Germany .................. 197 06 237

[51] Int. Cl.$^7$ .................................................. G03C 7/333
[52] U.S. Cl. ...................... 430/504; 430/505; 430/551; 430/558
[58] Field of Search ................................ 430/551, 558, 430/504, 505

[56] References Cited

FOREIGN PATENT DOCUMENTS 297836  1/1989  European Pat. Off. .

*Primary Examiner*—Janet Baxter
*Assistant Examiner*—Amanda C. Walke
*Attorney, Agent, or Firm*—Connolly Bove Lodge & Hutz LLP

[57] ABSTRACT

A color photographic recording material which contains, on a support, at least one blue-sensitive silver halide emulsion layer with which a yellow coupler is associated, at least one green-sensitive silver halide emulsion layer with which a magenta coupler is associated, and at least one red-sensitive silver halide emulsion layer with which a cyan coupler is associated, as well as light-insensitive intermediate layers between the layers of different coolor-sensitivity, characterised in that it contains a pyrazolotriazole coupler as a magenta coupler in at least one green-sensitive silver halide emulsion layer, and in at least one of said layers it contains, as a DOP scavenger, a compound of formula I

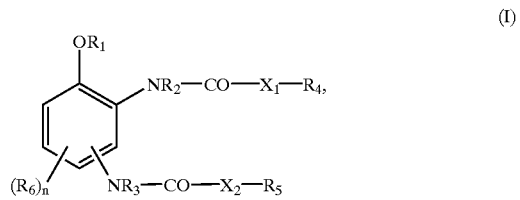

wherein $X_1, X_2$ represent a single bond, —O— or —NR$_7$—, $R_1$ represents hydrogen or a group which can split off under the conditions of chromogenic development, $R_2$ represents hydrogen or —CO—X$_1$—R$_4$, $R_3$ represents hydrogen or —CO—X$_2$—R$_5$, $R_4$, $R_5$ represent hydrogen, alkyl, alkenyl or a heterocyclic group, $R_6$ represents alkyl, aryl, acyl, alkoxy, aryloxy, acyloxy, halogen, —OH, —COOM, —SO$_3$M, —CN or —NO$_2$, $R_7$ represents hydrogen, alkyl, aryl or acyl, M represents hydrogen or a cation, and n represents 0, 1, 2 or 3 and wherein at least one $R_2$ or $R_3$ substituent is hydrogen, is distinguished by its improved stability under the effect of light.

11 Claims, No Drawings

COLOR PHOTOGRAPHIC RECORDING MATERIAL

This invention relates to a colour photographic recording material which contains a pyrazolotriazole coupler in one light-sensitive silver halide emulsion layer and which contains a new developer oxidation product (DOP) scavenger in the same layer or in a further layer.

It is known that coloured photographic images can be produced by chromogenic development, i.e. by developing silver halide emulsion layers, which are exposed image by image, in the presence of suitable colour couplers by means of suitable colour-forming developer substances—which are termed colour developers, wherein the oxidation product of the developer substances which is formed, corresponding to the silver image, reacts with the colour coupler thereby forming a dye image. Aromatic compounds which contain primary amino groups, particularly compounds of the p-phenylenediamine type, are, customarily used as colour developers.

Pyrazolone couplers are usually employed for the production of magenta dye image formers. The image dyes obtained from these pyrazolone couplers often do not exhibit ideal absorption. A feature which is particularly troublesome is the yellow secondary colour density, which makes the use of masking couplers or the employment of other masking techniques necessary in order to produce brilliant colours in the photographic image. A certain improvement in this respect can be obtained by the use of 3-anilinopyrazolone couplers. The colour reproduction still always leaves something to be desired, however.

Pyrazoles which are condensed with 5-membered heterocycles—which are termed pyrazoloazoles—can also be used as magenta couplers. The advantage of these compared with simple pyrazoles is that they possess colours which have a higher resistance to formalin and purer absorption spectra (EP-A-178 789).

A considerable problem when employing the frequently used pyrazolotriazole magenta couplers is the low stability of the image dyes which are obtained under the effect of light.

Investigations which have now been performed have confirmed that this effect is due in part to the DOP scavengers which are customarily used in the light-insensitive intermediate layers of a colour photographic material. These compounds are preferably hydroquinone compounds which are substituted by long-chain or voluminous alkyl groups or by an acylamino radical which imparts hydrophobic properties, or are di-sulphonamidophenols (EP-A-560 198).

The underlying object of the present invention is to improve the stability of a colour photographic recording material which contains a pyrazolotriazole magenta coupler.

It has now been found that the aforementioned object is achieved with a colour photographic recording material according to claim 1.

The present invention therefore relates to a colour photographic recording material which contains, on a support, at least one blue-sensitive silver halide emulsion layer with which a yellow coupler is associated, at least one green-sensitive silver halide emulsion layer with which a magenta coupler is associated, and at least one red-sensitive silver halide emulsion layer with which a cyan coupler is associated, as well as light-insensitive intermediate layers between the layers of different colour-sensitivity, characterised in that it contains a pyrazolotriazole coupler as a magenta coupler in at least one green-sensitive silver halide emulsion layer, and in at least one of said layers it contains, as a DOP scavenger, a compound of formula I

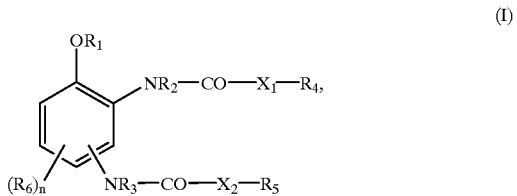

wherein
$X_1, X_2$ represent a single bond, —O— or —NR$_7$—,
$R_1$ represents hydrogen or a group which can split off under the conditions of chromogenic development,
$R_2$ represents hydrogen or —CO—X$_1$—R$_4$,
$R_3$ represents hydrogen or —CO—X$_2$—R$_5$,
$R_4$, $R_5$ represent hydrogen, alkyl, alkenyl or a heterocyclic group,
$R_6$ represents alkyl, aryl, acyl, alkoxy, aryloxy, acyloxy, halogen, —OH, —COOM, —SO$_3$M, —CN or —NO$_2$,
$R_7$ represents hydrogen, alkyl, aryl or acyl,
M represents hydrogen or a cation, and
n represents 0, 1, 2 or 3
and wherein at least one $R_2$ or $R_3$ substituent is hydrogen.

In a preferred embodiment of the invention, the symbols in formula I have the following meanings:
$X_1, X_2$ represent a single bond, —O— or —NR$_7$—,
$R_1$ represents hydrogen,
$R_2$ represents hydrogen or —CO—X$_1$—R$_4$,
$R_3$ represents hydrogen or —CO—X$_2$—R$_5$,
$R_4$, $R_5$ represent alkyl or aryl,
$R_6$ represents alkyl, acyl, alkoxy or chlorine,
$R_7$ represents hydrogen, alkyl or aryl,
M represents hydrogen or a cation, and
n represents 0 or 1, and
in addition, at least one $R_2$ or $R_3$ substituent is hydrogen and the —NR$_3$—CO—X$_2$—R$_5$ substituent is in the para or ortho position in relation to the —OR$_1$ substituent.

In a particularly preferred embodiment of the invention, the symbols in formula I have the following meanings:
$X_1, X_2$ represent a single bond, —O— or —NR$_7$—,
$R_1$, $R_2$, $R_3$ represent hydrogen,
$R_4$, $R_5$ represent alkyl or aryl,
$R_6$ represents alkyl, acyl, alkoxy or chlorine,
$R_7$ represents hydrogen, alkyl or aryl,
M represents hydrogen or a cation,
n represents 0 or 1, and
the —NR$_3$—CO—X$_2$—R$_5$ substituent is in the para position in relation to the —OR$_1$ substituent.

An alkyl or alkylene radical which is represented by $R_1$ to $R_7$ or which is contained therein may be a straight-chain, branched or cyclic radical.

A radical which is represented by $R_1$ to $R_7$ or which is contained therein may itself be substituted: possible substituents are alkyl, aryl, acyl, alkoxy, aryloxy, acyloxy, acylamino, alkylthio, arylthio, chloro, —OH, —COOM, —SO$_3$M, —CN, —NO$_2$ or —N(R$_4$)$_2$. If $R_4$ and $R_5$ are alkyl radicals, they may be substituted in a manner such that their definition also encompasses polymeric compounds. An acyl radical may be derived from an aliphatic or aromatic carboxylic or sulphonic acid, from carbonic acid, a carbamidic acid or aminosulphuric acid, or from a sulphinic, phosphonic or phosphoric acid.

Adjacent $R_1$ to $R_7$ radicals may form a heterocyclic 5- to 8-membered ring. In this connection, the term "adjacent" means that the radicals are not separated by more than four bonds.

Alkoxycarbonyl, -halogenoacyl and nitrobenzoyl groups are examples of groups which can split off under the conditions of chromogenic development.

Examples of suitable DOP scavengers of formula I are given below.

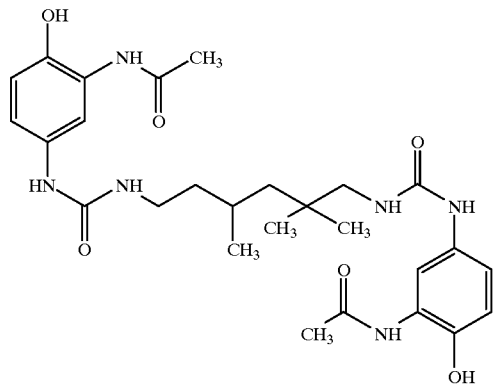
I-1

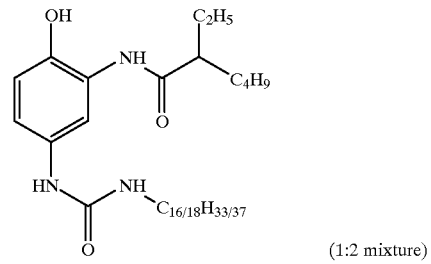
I-2
(1:2 mixture)

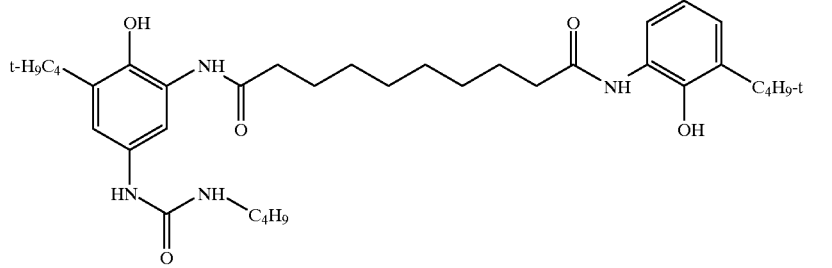
I-3

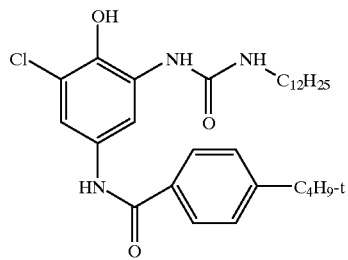
I-4

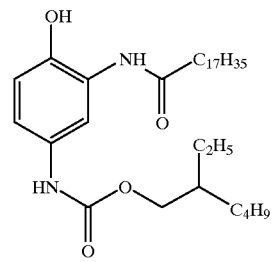
I-5

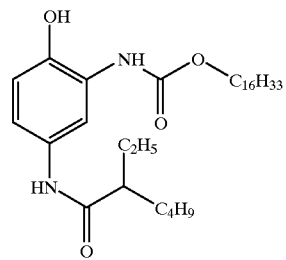
I-6

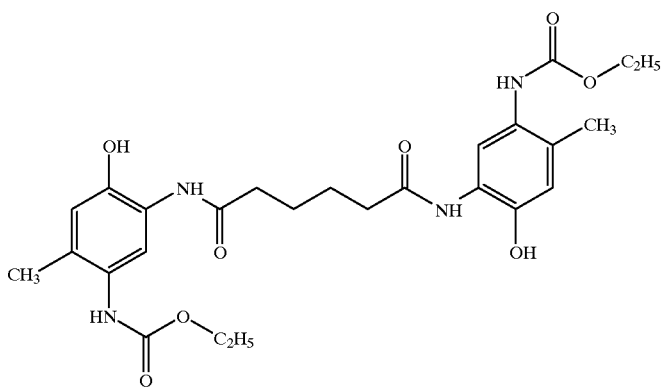
I-7
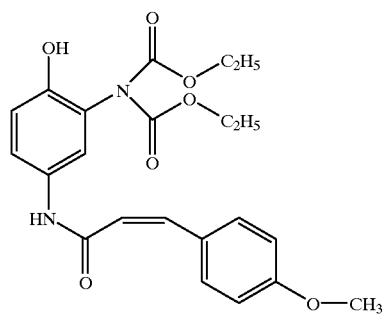
I-8
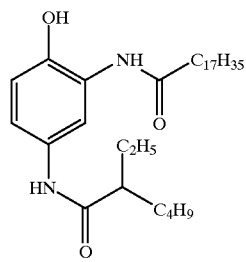
I-10
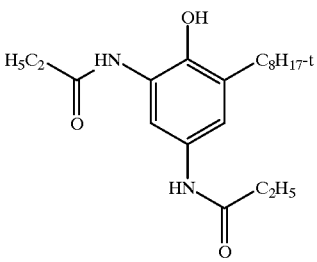
I-9
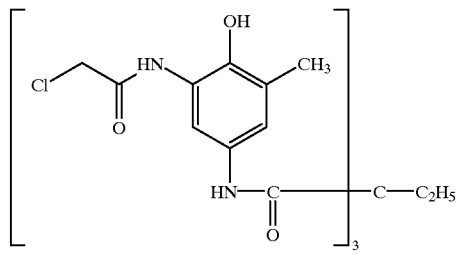
I-12
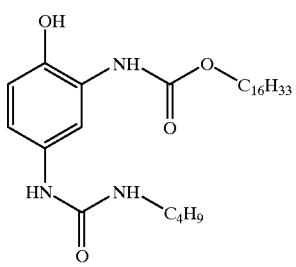
I-11
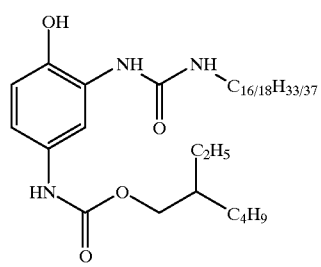
I-14
(1:2 mixture)
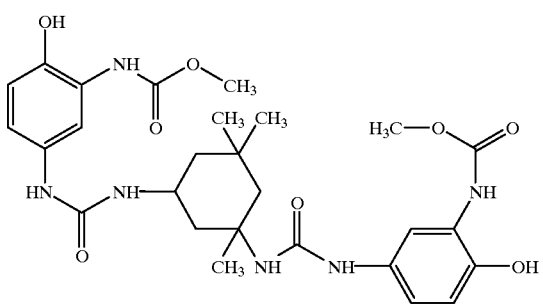
I-13
I-15

I-16
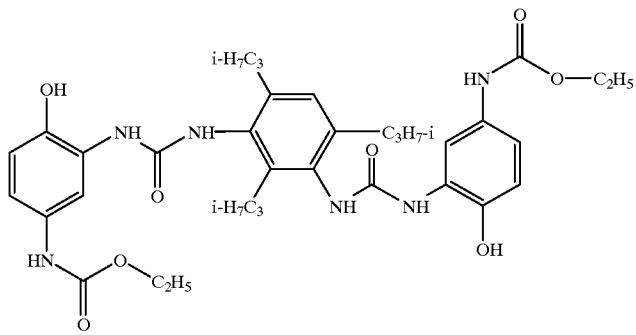
I-17
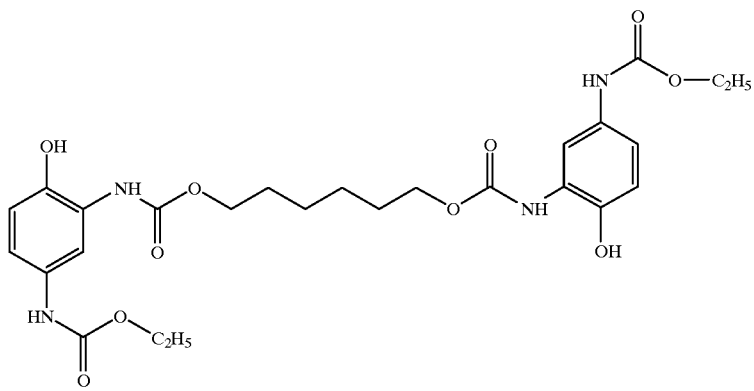
I-18
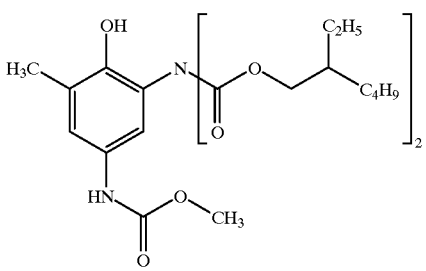
I-19
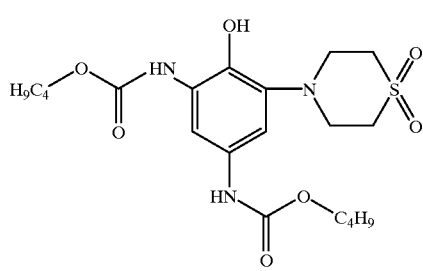
I-20
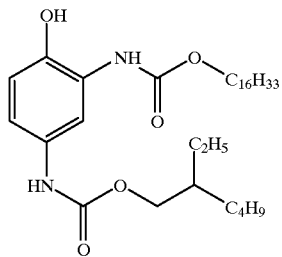
I-21
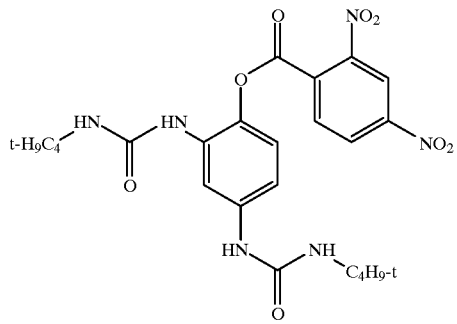

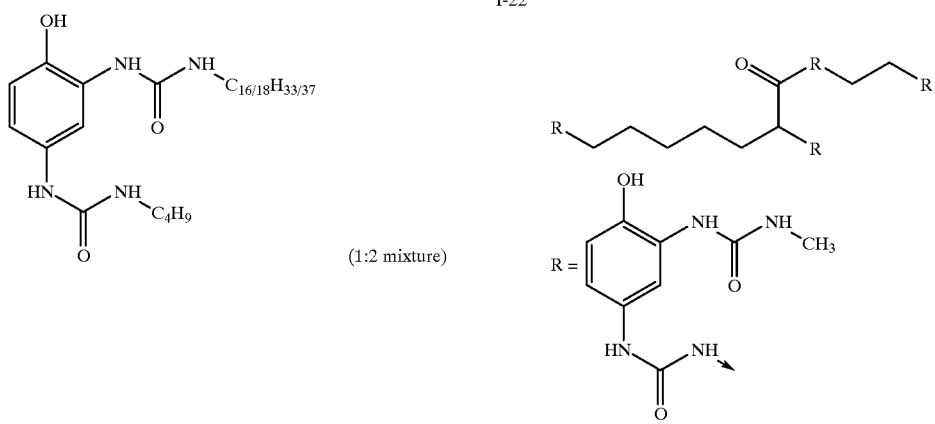
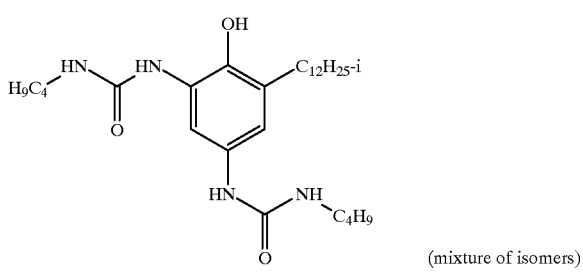
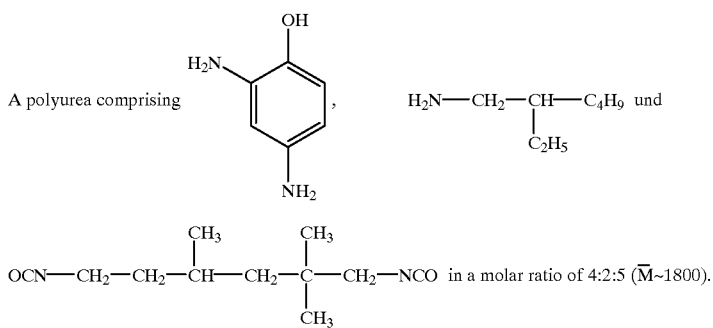
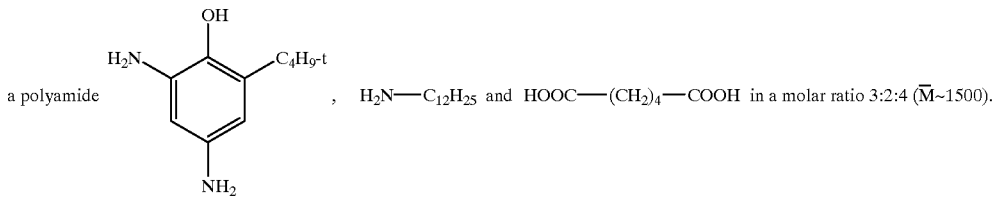
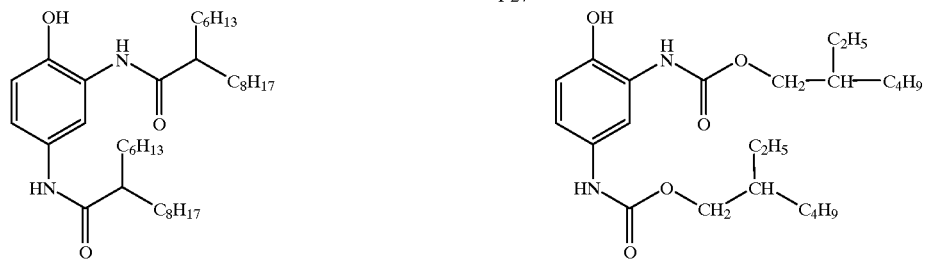

I-29
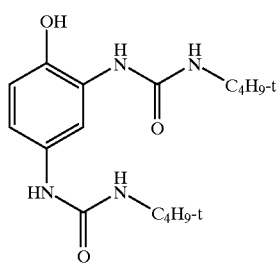

I-30
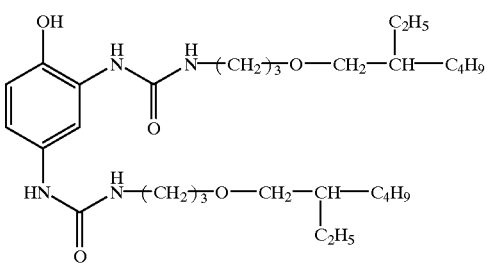

I-31
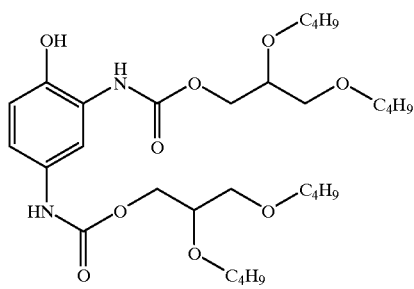

I-32
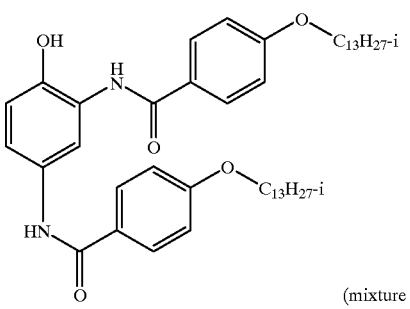

(mixture of isomers)

The DOP scavengers of formula I are usually employed in an amount of 10 to 1000 mg/m² per layer in the colour photographic material. Amounts of 20 to 400 g/m² are preferably used.

In a further preferred embodiment of the invention, the colour photographic recording material contains the DOP scavenger of formula I in at least one light-insensitive intermediate layer.

Therefore, a colour photographic recording material is particularly preferred which contains a pyrazolotriazole coupler as a magenta coupler in at least one green-sensitive silver halide emulsion layer and which contains a compound of formula I as a DOP scavenger in at least one intermediate layer adjacent to this layer.

The compounds of formula I can be prepared analogously to the method described in EP-A-98 072 for disulphonamides. The synthesis of compound I-2 is described below as an illustration.

Synthesis of I-2

1) 2-(2-ethylhexanoylamino)-4-nitrophenol (preliminary product 1)

77 g 2-amino-4-nitrophenol were dissolved in 1600 ml pyridine. 81 g 2-ethylhexanoic acid chloride were added at 15 C. over 1 hour and the batch was subsequently heated at 35 C. for 5 hours. 250 ml methylene chloride and 700 ml water were added thereto, and the organic phase was washed with water and dilute hydrochloric acid and dried over $Na_2SO_4$, and the solvent was distilled off. The crude product was purified by means of column chromatography (silica gel 60, mobile phase toluene/ethyl acetate (4:1)) and was recrystallised from aqueous ethanol: 39 g of yellow solid with a melting point of 151 to 152 C.

2) 4-amino-2-(2-ethylhexanoylamino)-phenol (preliminary product 2)

39 g of preliminary product 1 were hydrogenated with $H_2$/Raney nickel in 200 ml ethanol. The hydrogenation was conducted over a period of 2 hours and within a temperature range from 20 to 40 C. at a pressure of 2. $10^6$ Pa. The catalyst was filtered off under suction and 400 ml water were added. The dried, oily product (37 g) which was separated was reacted further without additional purification.

3) I-2

37 g of preliminary product 2 were dissolved in 1000 ml ethyl acetate. 42 g stearyl isocyanate were added thereto at room temperature and the batch was stirred for 6 hours. The product was filtered off under suction and was recrystallised from ethanol: 36 g of light grey solid.

The pyrazolotriazole magenta couplers are usually employed in a total amount of 50 to 800 mg/m², particularly 100 to 400 mg/m².

The preferred pyrazolotriazole couplers are those of formula II

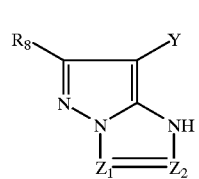

(II)

wherein $R_8$ represents hydrogen, halogen, alkyl, aryl, a heterocyclic group, cyano, alkoxy, acyloxy, carbamoyloxy, acylamino, or a polymer residue, Y represents hydrogen or a group which can split off under the conditions of chromogenic development, one of the $Z_1$ and $Z_2$ radicals represents a nitrogen atom and the other represents —$CR_9$, and $R_9$ has the same meaning as $R_8$, wherein one of the $R_8$ and $R_9$ radicals is a ballast group or is substituted by a ballast group, wherein the ballast group may also be a polymer residue.

In a preferred embodiment,
Y represents hydrogen, chlorine, alkyl, aryl, acyl or
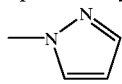
In another preferred embodiment, $R_8$ and $R_9$ together comprise at least 15 C atoms.
Examples of suitable pyrazolotriazole couplers of formula II are given below.
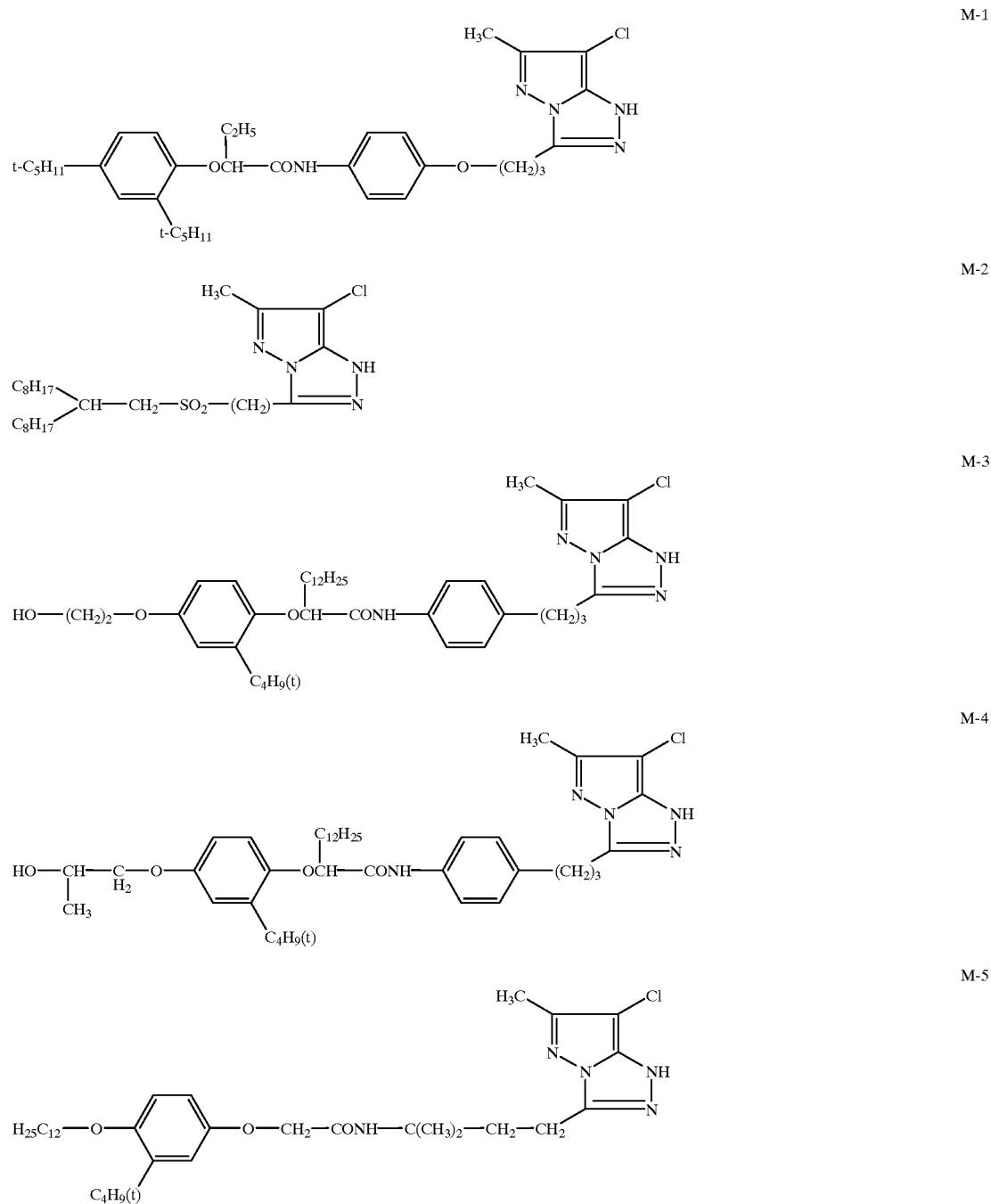

-continued
M-6
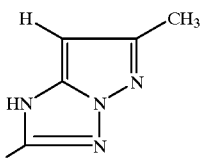
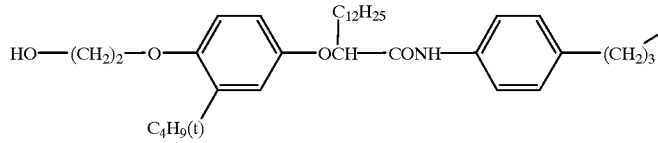
M-7
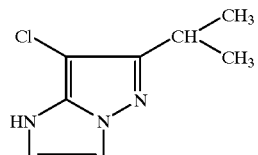
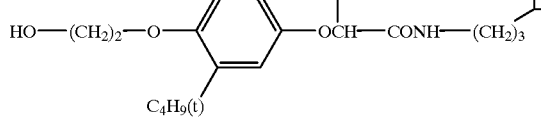
M-8
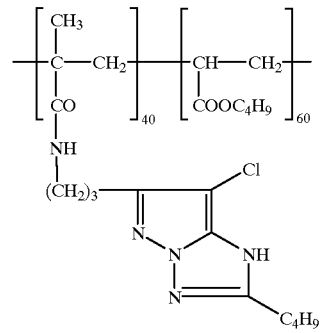
M-9
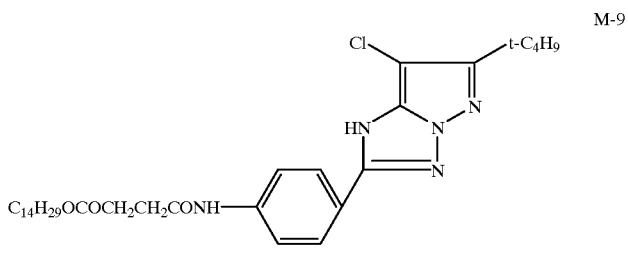
M-10
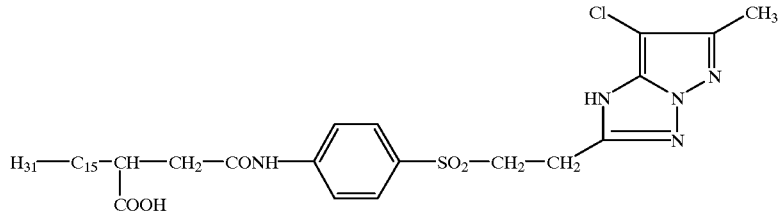
M-11
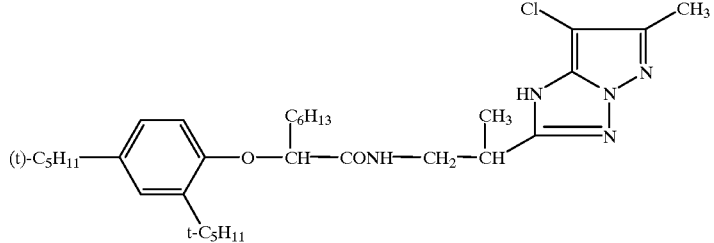

-continued

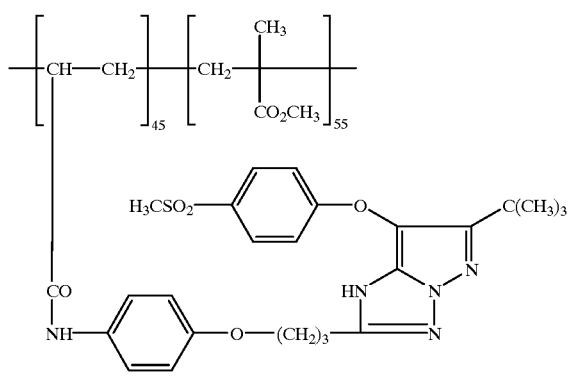

M-12

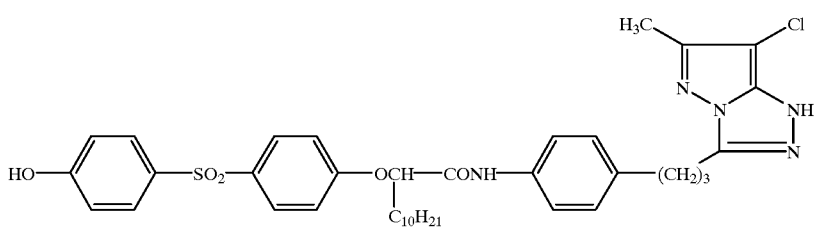

M-13

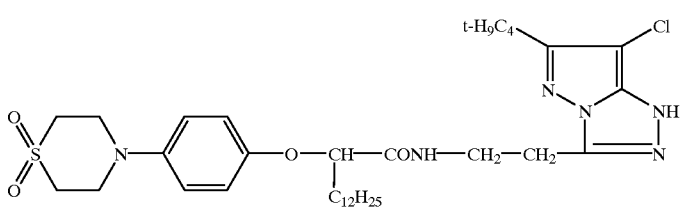

M-14

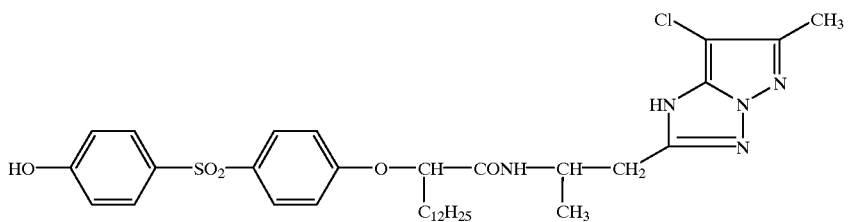

M-15

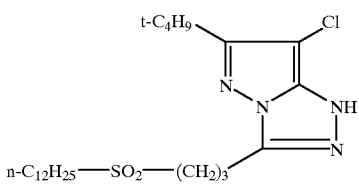

M-16

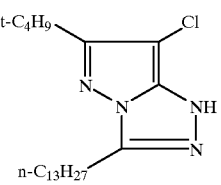

M-17

The use of compounds of formulae I and II in photographic materials is known. U.S. Pat. No. 3,291,609 describes the use of acylaminophenols as what are termed developer precursor compounds in black and white materials.

DE-A-25 36 401 (U.S. Pat. No. 4,083,721) describes the use of special acylamino- and diacylaminophenols as cyan colour couplers in a photographic material which does not contain a pyrazolotriazole magenta coupler.

DE-A-42 36 748 discloses photographic materials which contain pyrazolotriazole magenta couplers and acylaminophenols together in a light-sensitive silver halide emulsion layer.

However, it is completely surprising, and cannot be inferred from the above documents, that the use in a photographic material of the diacylaminophenols which are now described and which are excellent DOP scavengers on account of their particular substitution pattern leads to an improvement in stability. This effect is particularly pronounced if these new DOP scavengers are located in a light-insensitive layer.

Examples of colour photographic materials include colour negative films, colour reversal films, colour positive films, colour photographic paper, colour reversal photographic paper, and colour-sensitive materials for the colour diffusion transfer process or for the silver colour-bleaching process.

The photographic materials consist of a support on which at least one light-sensitive silver halide emulsion layer is deposited. Thin films and foils are particularly suitable as supports. A review of support materials and of the auxiliary layers which are deposited on the front and back thereof is given in Research Disclosure 37254, Part 1 (1995), page 285.

The material according to the invention preferably has a reflecting support.

Colour photographic materials usually contain at least one red-sensitive, at least one green-sensitive and at least one blue-sensitive silver halide emulsion layer, and optionally contain intermediate layers and protective layers also.

Depending on the type of photographic material, these layers may be arranged differently. This will be illustrated for the most important products:

Colour photographic films such as colour negative films and colour reversal films comprise, in the following sequence on their support: 2 or 3 red-sensitive, cyan-coupling silver halide emulsion layers, 2 or 3 green-sensitive, magenta coupling silver halide emulsion layers, and 2 or 3 blue-sensitive, yellow-coupling silver halide emulsion layers. The layers of identical spectral sensitivity differ as regards their photographic speed, wherein the less sensitive partial layers are generally disposed nearer the support than are the more highly sensitive partial layers.

The options for different layer arrangements and their effects on photographic properties are described in J. Inf. Rec. Mats., 1994, Vol. 22, pages 183–193.

Colour photographic paper, which as a rule is less sensitive to light than is colour photographic film, usually comprises the following layers on the support, in the following sequence: a blue-sensitive, yellow-coupling silver halide emulsion layer, a green-sensitive, magenta coupling silver halide emulsion layer, and a red-sensitive, cyan-coupling silver halide emulsion layer.

Departures from the number and arrangement of the light-sensitive layers may be effected in order to achieve defined results. For example, all the high-sensitivity layers may be combined to form a layer stack and all the low-sensitivity layers may be combined to form another layer stack in a photographic film, in order to increase the sensitivity (DE-25 30 645).

The essential constituents of the photographic emulsion layer are the binder, the silver halide grains and colour couplers.

Information on suitable binders is given in Research Disclosure 37254, Part 2 (1995), page 286.

Information on suitable silver halide emulsions, their production, ripening, stabilisation and spectral sensitisation, including suitable spectral sensitisers, is given in Research Disclosure 37254, Part 3 (1995), page 286, and in Research Disclosure 37038, Part XV (1995), page 89.

Colour photographic materials which exhibit camera-sensitivity usually contain silver bromide-iodide emulsions, which may also optionally contain small proportions of silver chloride. Photographic copier materials contain either silver chloride-bromide emulsions comprising up to 80 mole % AgBr, or silver chloride-bromide emulsions comprising more than 95 mole % AgCl.

Information on colour couplers is to be found in Research Disclosure 37254, Part 4 (1995), page 288, and in Research Disclosure 37038, Part II (1995), page 80. The maximum absorption of the dyes formed from the couplers and from the colour developer oxidation product preferably falls within the following ranges: yellow couplers 430 to 460 nm, magenta couplers 540 to 560 nm, cyan couplers 630 to 700 nm.

In order to improve sensitivity, granularity, sharpness and colour separation, compounds are frequently used in colour photographic films which on reaction with the developer oxidation product release compounds which are photographically active, e.g. DIR couplers, which release a development inhibitor.

Information on compounds such as these, particularly couplers, is to be found in Research Disclosure 37254, Part 5 (1995), page 290, and in Research Disclosure 37038, Part XIV (1995), page 86.

The colour couplers, which are mostly hydrophobic, and other hydrophobic constituents of the layers also, are usually dissolved or dispersed in high-boiling organic solvents. These solutions or dispersions are then emulsified in an aqueous binder solution (usually a gelatine solution), and after the layers have been dried are present as fine droplets (0.05 to 0.8 µm diameter) in the layers.

Suitable high-boiling organic solvents, methods of introduction into the layers of a photographic material, and other methods of introducing chemical compounds into photographic layers, are described in Research Disclosure 37254, Part 6 (1995), page 292.

The light-insensitive intermediate layers which are generally disposed between layers of different spectral sensitivity may contain media which prevent the unwanted diffusion of developer oxidation products from one light-sensitive layer into another light-sensitive layer which has a different spectral sensitivity.

Suitable compounds (white couplers, scavengers or DOP scavengers) are described in Research Disclosure 37254, Part 7 (1995), page 292, and in Research Disclosure 37038, Part III (1995), page 84.

Examples of prior art DOP scavengers which are particularly suitable for use in a photographic material together with the DOP scavengers according to the invention are given below.

EF-1

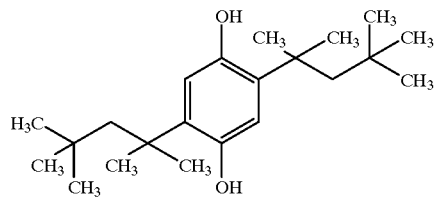

EF-2

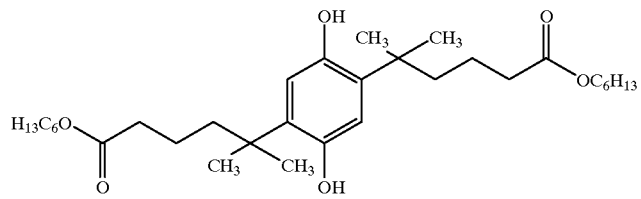

-continued
EF-3 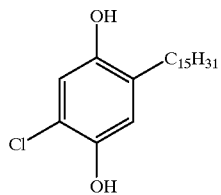
EF-4 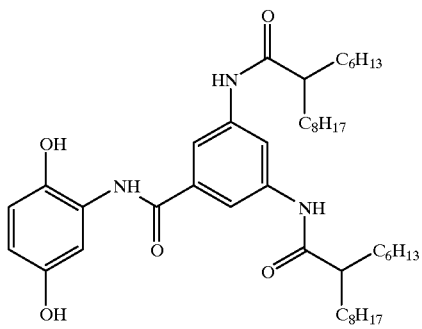
EF-5 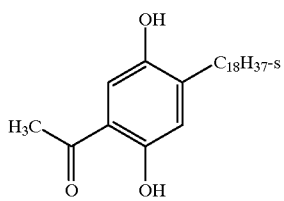
EF-6 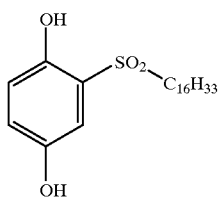
EF-7 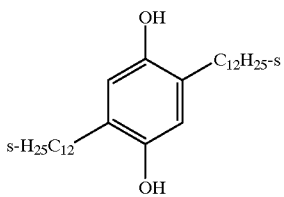
EF-8 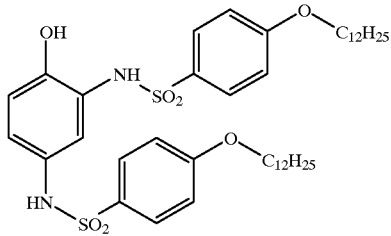
EF-9 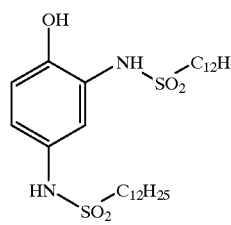
EF-10 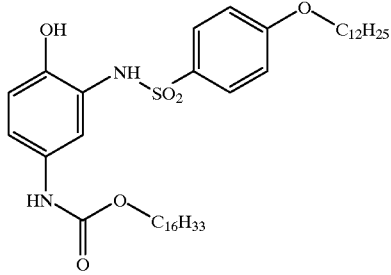
EF-11 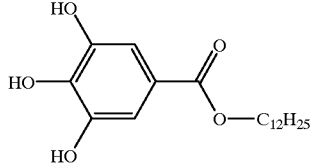
EF-12 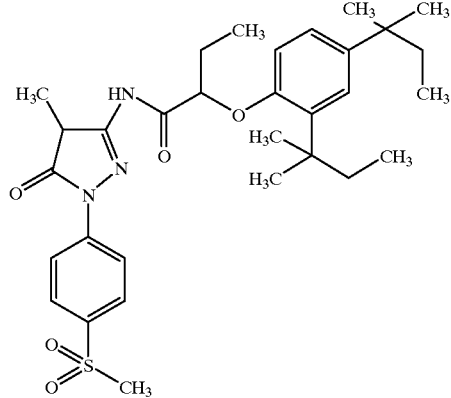

-continued

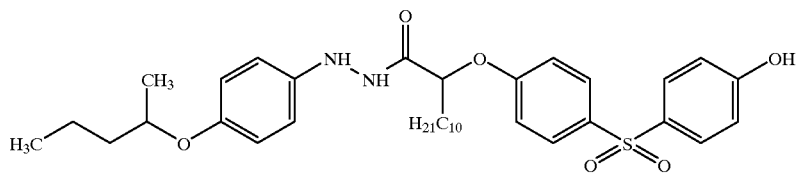
EF-13

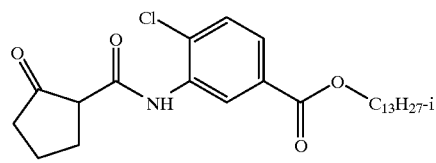
EF-14

The photographic material may additionally contain compounds which absorb UV light, optical brighteners, spacers, filter dyes, formalin scavengers, light stabilisers, antioxidants, $D_{min}$ dyes, additives for improving dye-, coupler- and whiteness-stability and for reducing colour fogging, plasticisers (latices), biocides and other substances.

Suitable compounds are described in Research Disclosure 37254, Part 8 (1995), page 292, and in Research Disclosure 37038, Parts IV, V, VI, VII, X, XI and XIII (1995), page 84 et seq.

The layers of colour photographic material are usually hardened, i.e. the binder which is used, preferably gelatine, is crosslinked by suitable chemical methods.

Suitable hardener substances are described in Research Disclosure 37254, Part 9 (1995), page 294, and in Research Disclosure 37038, Part XII (1995), page 86.

After image-by-image exposure, colour photographic materials are processed by different methods corresponding to their character. Details on the procedures used and the chemicals required therefor are published in Research Disclosure 37254, Part 10 (1995), page 294, and in Research Disclosure 37038, Parts XVI to XXIII (1995), page 95 et seq., together with examples of materials.

Example 1

A colour photographic recording material was produced by depositing the following layers in the given sequence on a film base comprising paper coated on both sides with polyethylene. The quantitative data are given with respect to 1 m² in each case. The corresponding amounts of $AgNO_3$ are quoted for silver halide deposition.

Layer Structure 1

Layer 1 (substrate layer)
    0.10 g gelatine
Layer 2 (blue-sensitive layer)
    blue-sensitive silver halide emulsion (99.5 mole % chloride, 0.5 mole % bromide, average grain diameter 0.9 μm), comprising
    0.50 g $AgNO_3$, with
    1.25 g gelatine
    0.42 g yellow coupler Y-1
    0.18 g yellow coupler Y-2
    0.50 g oil former OF-1
    0.10 g stabiliser ST-1
    0.70 mg blue sensitiser BS-1
    0.30 mg stabiliser ST-2
Layer 3 (intermediate layer)
    1.10 g gelatine
    0.06 g DOP scavenger EF-1
    0.06 g DOP scavenger EF-2

-continued 0.12 g tricresyl phosphate (TCP)
Layer 4 (green-sensitive layer)
    green-sensitive silver halide emulsion (99.5 mole % chloride, 0.5 mole % bromide, average grain diameter 0.47 μm), comprising 0.40 g $AgNO_3$, with
    0.77 g gelatine
    0.41 g magenta coupler M-1
    0.06 g stabiliser ST-3
    0.12 g DOP scavenger EF-2
    0.34 g dibutyl phthalate (DBP)
    0.70 mg green sensitiser GS-1
    0.50 mg stabiliser ST-4
Layer 5 (UV protection layer)
    0.95 g gelatine
    0.30 g UV absorber UV-1
    0.03 g DOP scavenger EF-1
    0.03 g DOP scavenger EF-2
    0.15 g oil former OF-2
    0.15 g TCP
Layer 6 (red-sensitive layer)
    red-sensitive silver halide emulsion (99.5 mole % chloride, 0.5 mole % bromide, average grain diameter 0.5 μm), comprising
    0.30 g $AgNO_3$, with
    1.0 g gelatine
    0.46 g cyan coupler C-1
    0.46 g TCP
    0.03 mg red sensitiser RS-1
    0.60 mg stabiliser ST-5
    0.30 g UV absorber UV-2
Layer 7 (UV protection layer)
    0.30 g gelatine
    0.10 g UV absorber UV-3
    0.15 g oil former OF-3
Layer 8 (protective layer)
    0.90 g gelatine
    0.05 g optical brightener WT-1
    0.07 g mordant (polyvinylpyrrolidone)
    1.20 mg silicone oil
    2.50 mg spacer (polymethyl methacrylate, average particle size 0.8 μm)
    0.30 g hardener H-1

Compounds used in the examples:

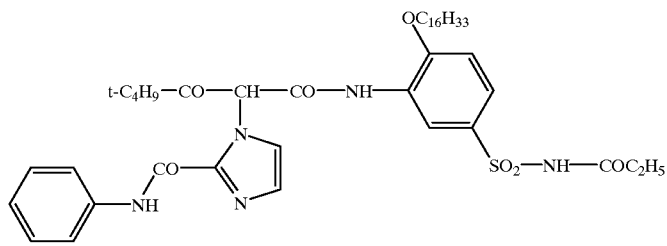
Y-1
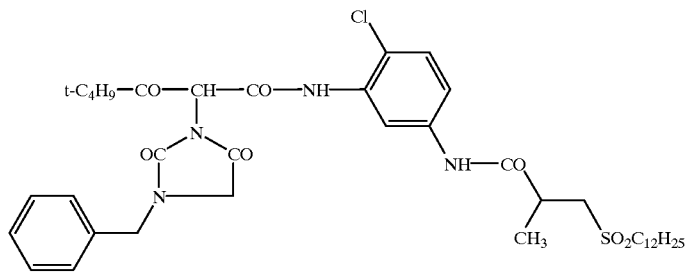
Y-2
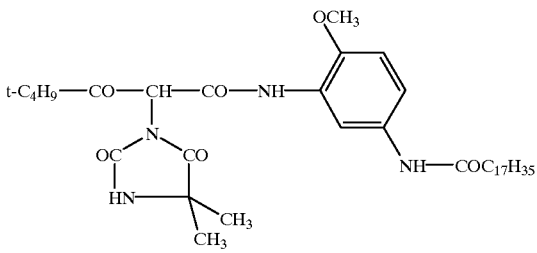
Y-3
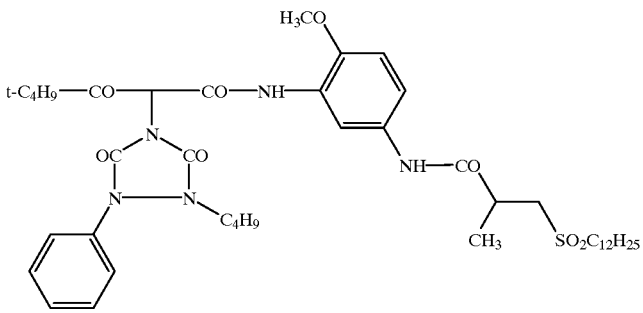
Y-4
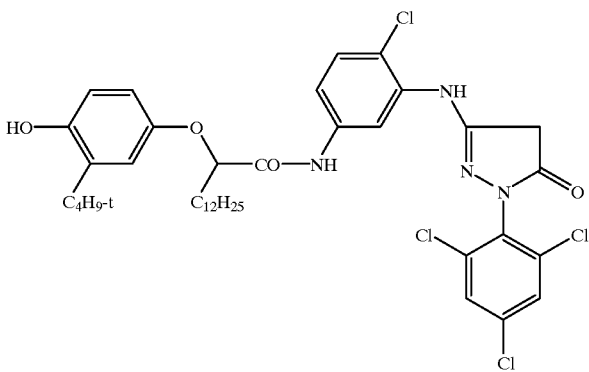
M-1

-continued
M-2
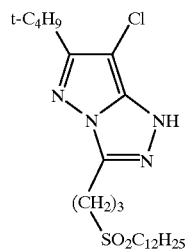
M-3
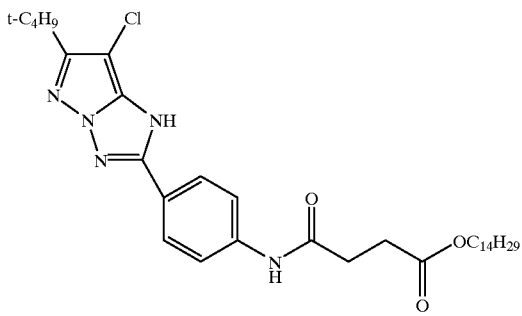
C-1
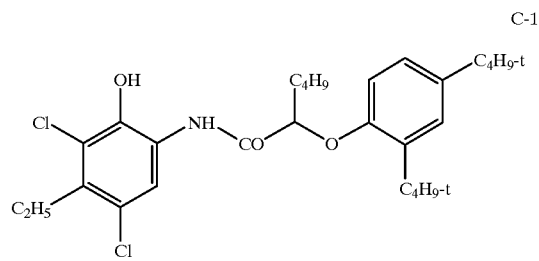
C-2
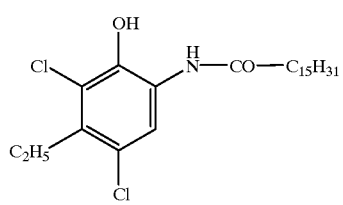
BS-1
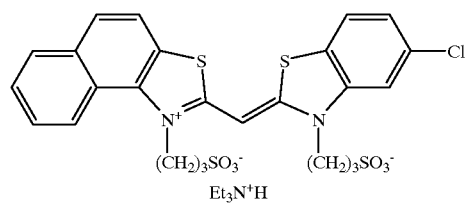
GS-1
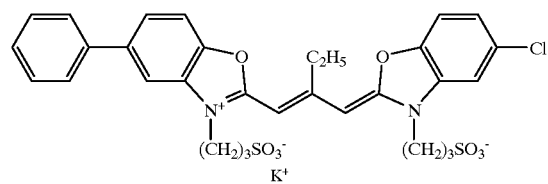
RS-1
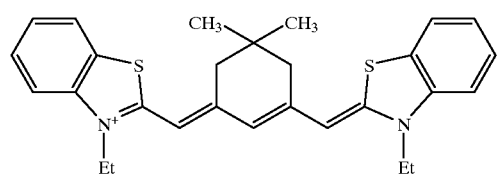
ST-1
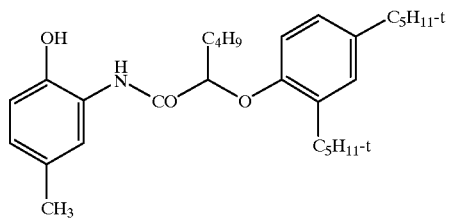
ST-2
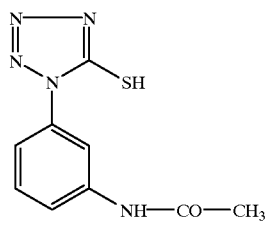
ST-3
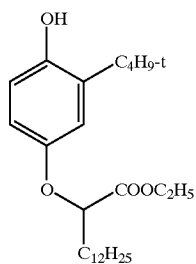
ST-4
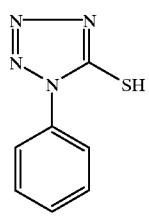
ST-5
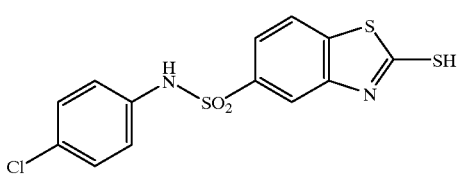

ST-6
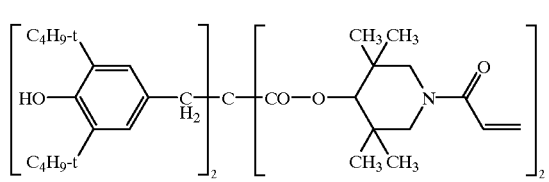
ST-7
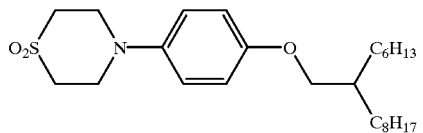
ST-8
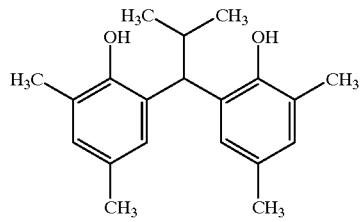
ST-8
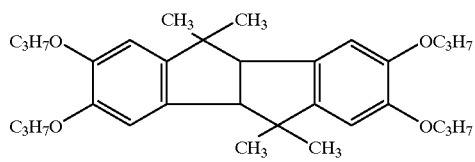
ST-10
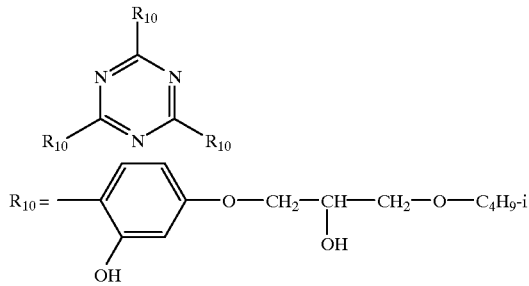
OF-1
Polyester aus $HO_2C\text{---}(CH_2)_4\text{---}CO_2H$,
$HOCH_2\text{---}C(CH_3)_2\text{---}CH_2OH$ und
$HO\text{---}C_{10}H_{21}\text{-i}$
$\eta(20°\ C.): 4000\text{--}5000\ mPa\cdot s$
$n_D(20°\ C.): 1.464\text{--}1.467$
OF-2
$\text{---}(CH_2\text{---}CH_2\text{---}CO_2\text{---}C_9H_{19}\text{-i})_2$
OF-3
$O\!=\!P(O\text{---}CH_2\text{---}CH(C_2H_5)\text{---}C_4H_9)_3$
UV-1
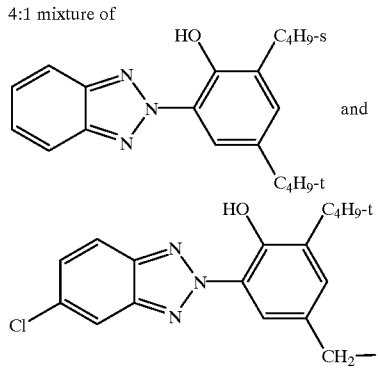
UV-2
4:1 mixture of
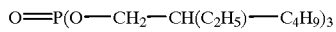
and
$R_{11} = \text{---}C_8H_{17}\text{-n}$
$R_{12} = \text{---}CH_2\text{---}CH(C_2H_5)\text{---}C_4H_9$
UV-3
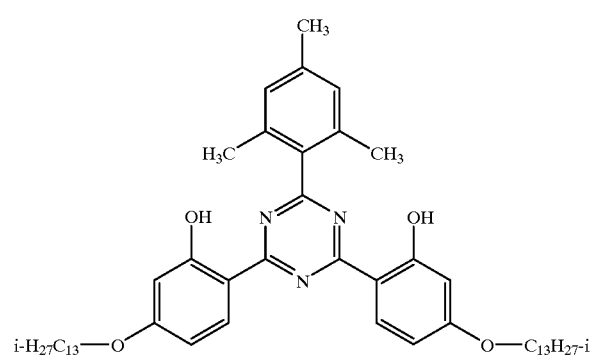

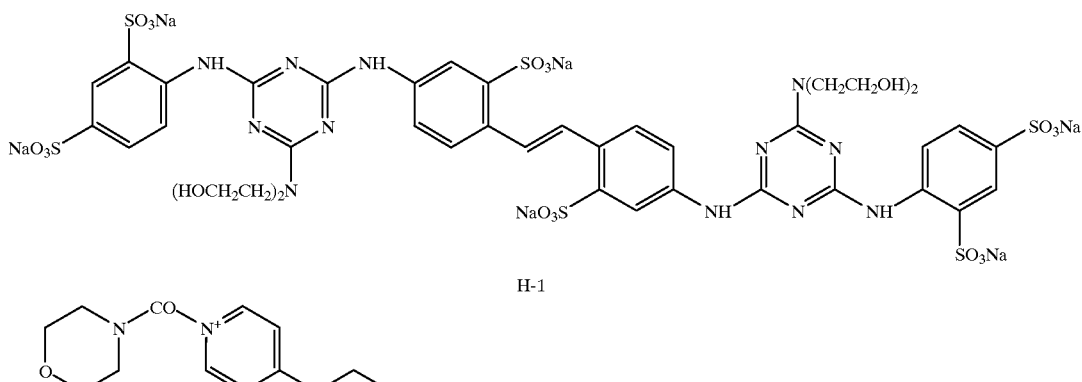

WT-1

H-1

Layer Structures 2 to 18

For layer structures 2 to 18, the compounds given in Table 1 were interchanged in layers 2 to 6. Moreover, when M-2 and M-3 were used in layer 4 the amount of silver in this layer was reduced to 0.25 g or 0.20 g.

All the samples were exposed through a stepped photometric absorption wedge and a U-531 filter (magenta colour separation), and were subsequently processed as follows:

a) Colour developer—45 sec—35 C.

| | |
|---|---|
| tetraethylene glycol | 20.0 g |
| N,N-diethylhydroxylamine | 4.0 g |
| N-ethyl-N-(2-methanesulphonamidoethyl)-4-amino-3-methylbenzene sulphate | 5.0 g |
| potassium sulphite | 0.2 g |
| potassium carbonate | 30.0 g |
| polymaleic anhydride | 2.5 g |
| hydroxyethanediphosphonic acid | 0.2 g |
| optical brightener (a 4,4-diaminostilbene- | 2.0 g |

-continued

| | |
|---|---|
| sulphonic acid derivative) | |
| potassium bromide | 0.02 g | made up to 1000 ml with water; pH adjusted to pH 10.2 with KOH or $H_2SO_4$.

b) Bleach-hardener—45 sec—35 C.

| | |
|---|---|
| ammonium thiosulphate | 75.0 g |
| sodium hydrogen sulphite | 13.5 g |
| ethylenediaminetetraacetic acid (iron ammonium salt) | 45.0 g | made up to 1000 ml with water; pH adjusted to pH 6.0 with ammonia (25% by weight) or acetic acid.

c) Washing—90 sec—33 C.

d) Drying

TABLE 1

(C = comparison; I = invention; numbers in parentheses: amount of deposit in mg/m²)

| Layer structure | Layer 2 yellow coupler | Layer 2 stabiliser | Layer 3 DOP scavenger | Layer 4 magenta coupler | Layer 4 stabiliser/DOP scavenger | Layer 5 oil-former | Layer 5 DOP scavenger | Layer 6 cyan coupler |
|---|---|---|---|---|---|---|---|---|
| 1 (C) | Y-1/Y-2 | ST-1 | EF-1/EF-2 | M-1 | ST-3/EF-2 | DBP | EF-1/EF-2 | C-1 |
| 2 (C) | " | " | V-1 (120) | " | " | " | V-1 (60) | " |
| 3 (C) | " | " | I-6 (120) | " | " | " | I-6 (60) | " |
| 4 (C) | " | " | I-14 (120) | " | " | " | I-14 (60) | " |
| 5 (C) | Y-3 (550) | ST-6 (150) | EF-1/EF-2 (70/70) | M-2 (210) | ST-7/ST-9 (150/75) | OF-2/DBP (200/100) | EF-1/EF-2 (70/70) | C-1 (350) |
| 6 (C) | " | " | V-2 (140) | " | " | " | V-2 (140) | " |
| 7 (C) | " | " | V-3 (140) | " | " | " | V-3 (140) | " |
| 8 (C) | " | " | V-1 (140) | " | " | " | V-1 (140) | " |
| 9 (I) | " | " | I-2 (140) | " | " | " | I-2 (140) | " |
| 10 (I) | " | " | I-20 (140) | " | " | " | I-20 (140) | " |
| 11 (I) | " | " | I-5 (140) | " | " | " | I-5 (140) | " |
| 12 (I) | " | " | I-13 (140) | " | " | " | I-13 (140) | " |
| 13 (C) | Y-4 (500) | ST-1 (125) | EF-1 (50) | M-3 (140) | ST-8/ST-10 (15/15) | TCP/OF-3 100/100 | EF-1 (50) | C-2 (280) |
| 14 (C) | " | " | V-2 (80) | " | " | " | V-2 (80) | " |
| 15 (I) | " | " | I-2 (80) | " | " | " | I-2 (80) | " |
| 16 (I) | " | " | I-4 (80) | " | " | " | I-4 (80) | " |
| 17 (I) | " | " | I-17 (80) | " | " | " | I-17 (80) | " |

TABLE 1-continued (C = comparison; I = invention; numbers in parentheses: amount of deposit in mg/m²)

| Layer structure | Layer 2 yellow coupler | stabiliser | Layer 3 DOP scavenger | magenta coupler | Layer 4 stabiliser/DOP scavenger | oil-former | Layer 5 DOP scavenger | Layer 6 cyan coupler |
|---|---|---|---|---|---|---|---|---|
| 18 (I) | " | " | I-25 (80) | " | " | " | I-25 (80) | " |
| 19 (C) | " | " | V-4 (80) | " | " | " | V-4 (80) | " |

The yellow and cyan secondary densities were subsequently each measured at $D_{magenta}=0.6$ and $D_{magenta}=1.5$. The results are shown in Table 2.

TABLE 2

| | Secondary densities (%) | | | | Fogging |
|---|---|---|---|---|---|
| Layer structure | at $D_{magenta}=0.6$ | | at $D_{magenta}=1.5$ | | |
| | yellow ND | cyan ND | yellow ND | cyan ND | yellow |
| 1 (C) | 23.4 | 6.6 | 24.2 | 7.9 | 0.120 |
| 2 (C) | 23.8 | 6.9 | 24.7 | 8.3 | 0.118 |
| 3 (C) | 23.3 | 6.6 | 24.2 | 7.9 | 0.121 |
| 4 (C) | 23.4 | 6.6 | 24.3 | 8.0 | 0.120 |
| 5 (C) | 21.8 | 6.1 | 22.5 | 7.1 | 0.110 |
| 6 (C) | 22.0 | 6.3 | 22.8 | 7.5 | 0.109 |
| 7 (C) | 21.6 | 5.8 | 22.2 | 6.7 | 0.195 |
| 8 (C) | 22.1 | 6.5 | 22.9 | 7.9 | 0.111 |
| 9 (I) | 21.8 | 6.1 | 22.6 | 7.1 | 0.112 |
| 10 (I) | 21.9 | 6.2 | 22.7 | 7.2 | 0.108 |
| 11 (I) | 22.0 | 6.2 | 22.8 | 7.3 | 0.110 |
| 12 (I) | 21.9 | 6.1 | 22.6 | 7.2 | 0.111 |
| 13 (C) | 21.9 | 5.4 | 22.2 | 6.3 | 0.105 |
| 14 (C) | 22.0 | 5.7 | 22.4 | 6.5 | 0.107 |
| 15 (I) | 21.9 | 5.6 | 22.3 | 6.4 | 0.106 |
| 16 (I) | 21.8 | 5.7 | 22.4 | 6.5 | 0.104 |
| 17 (I) | 21.8 | 5.5 | 22.1 | 6.1 | 0.104 |
| 18 (I) | 21.9 | 5.6 | 22.2 | 6.4 | 0.105 |
| 19 (C) | 26.3 | 10.8 | 28.4 | 11.7 | 0.106 |

C: comparison
I: invention

As shown in Table 2, the compounds according to the invention are equal to or superior to the comparison compounds as regards their effectiveness as DOP scavengers (with the exception of V-3). V-3 resulted in a significant increase in fogging, however.

EXAMPLE 2

Samples 5 to 16 were exposed to the light from a xenon lamp normalised with respect to daylight, and were irradiated at 15×10⁶ Lxh (test conditions: 30 C., 80% relative atmospheric humidity). The magenta light-stability was subsequently determined by means of the change in density. The results are shown in Table 3.

TABLE 3

| | Changes in density (%) | |
|---|---|---|
| Layer structure | $D_{magenta}=0.6$ | $D_{magenta}=1.4$ |
| 5 (C) | −86 | −67 |
| 6 (C) | −78 | −63 |
| 7 (C) | −75 | −60 |
| 8 (C) | −43 | −36 |
| 9 (I) | −44 | −36 |

TABLE 3-continued

| | Changes in density (%) | |
|---|---|---|
| Layer structure | $D_{magenta}=0.6$ | $D_{magenta}=1.4$ |
| 10 (I) | −46 | −39 |
| 11 (I) | −45 | −38 |
| 12 (I) | −42 | −34 |
| 13 (C) | −30 | −23 |
| 14 (C) | −31 | −23 |
| 15 (I) | −17 | −10 |
| 16 (I) | −18 | −9 |

C: comparison
I: invention

As shown in Table 3, the samples according to the invention exhibited the highest possible magenta dye stability. Only layer structure 8, comprising comparison compound V-1, was comparable with this. However, V-1 was less effective at preventing combined coupling than were the compounds according to the invention, and was therefore an inferior DOP scavenger (see Example 1 also).

The following comparison compounds were used in the examples:

V-I = EF-8

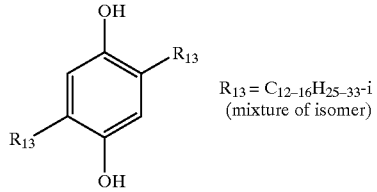

V-2

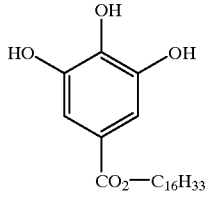

V-3

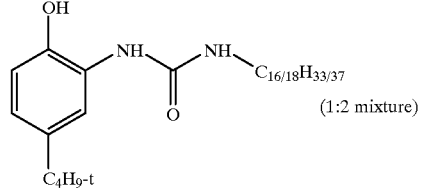

V-4

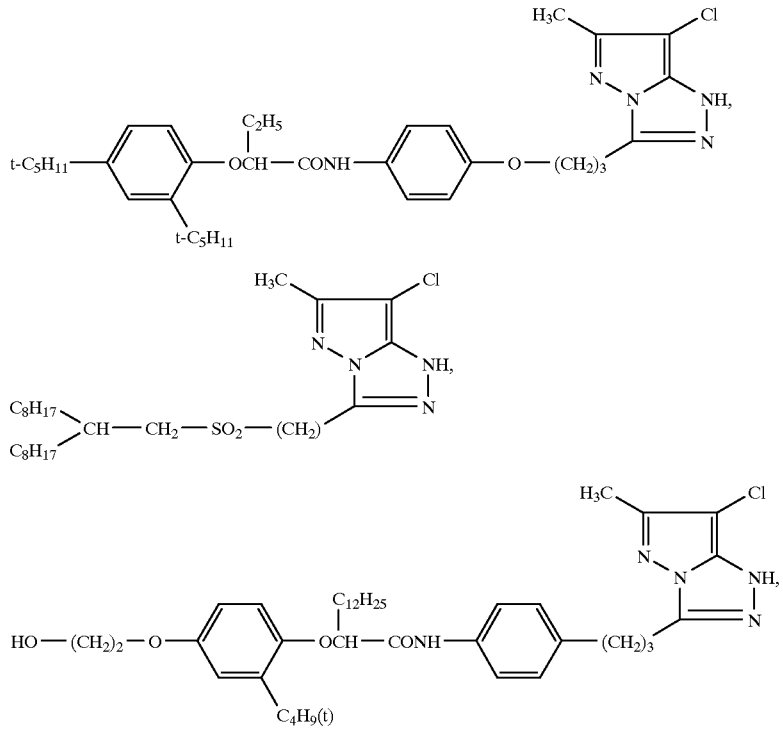

-continued
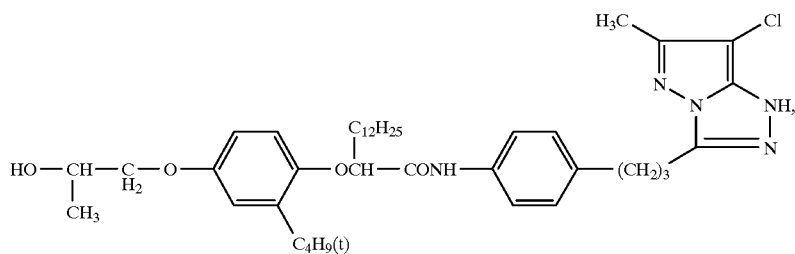
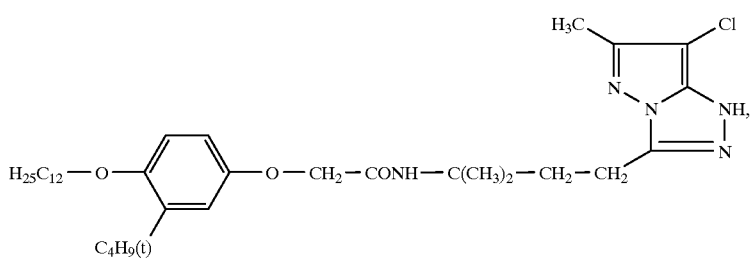
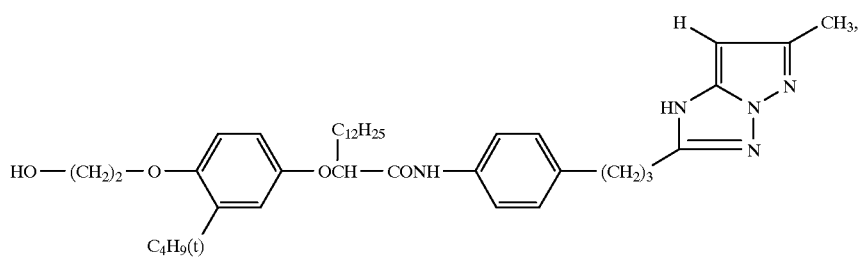
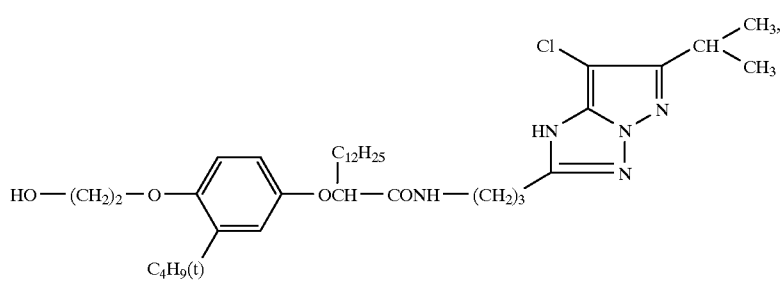
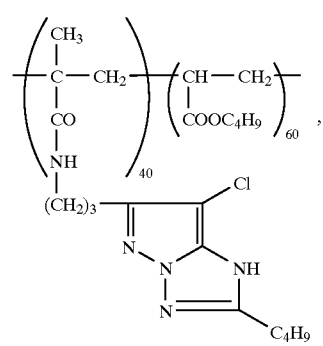
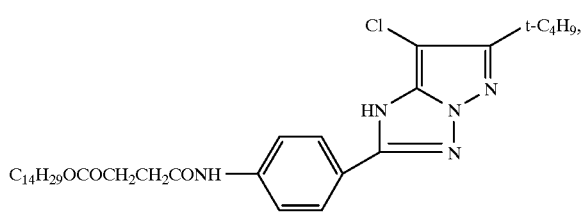
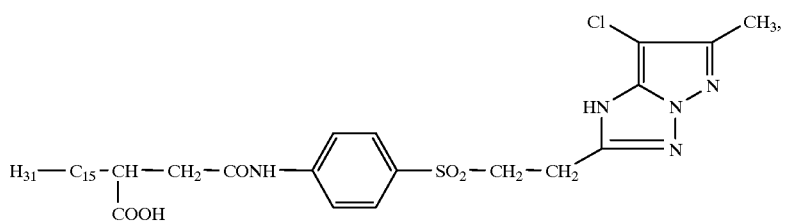

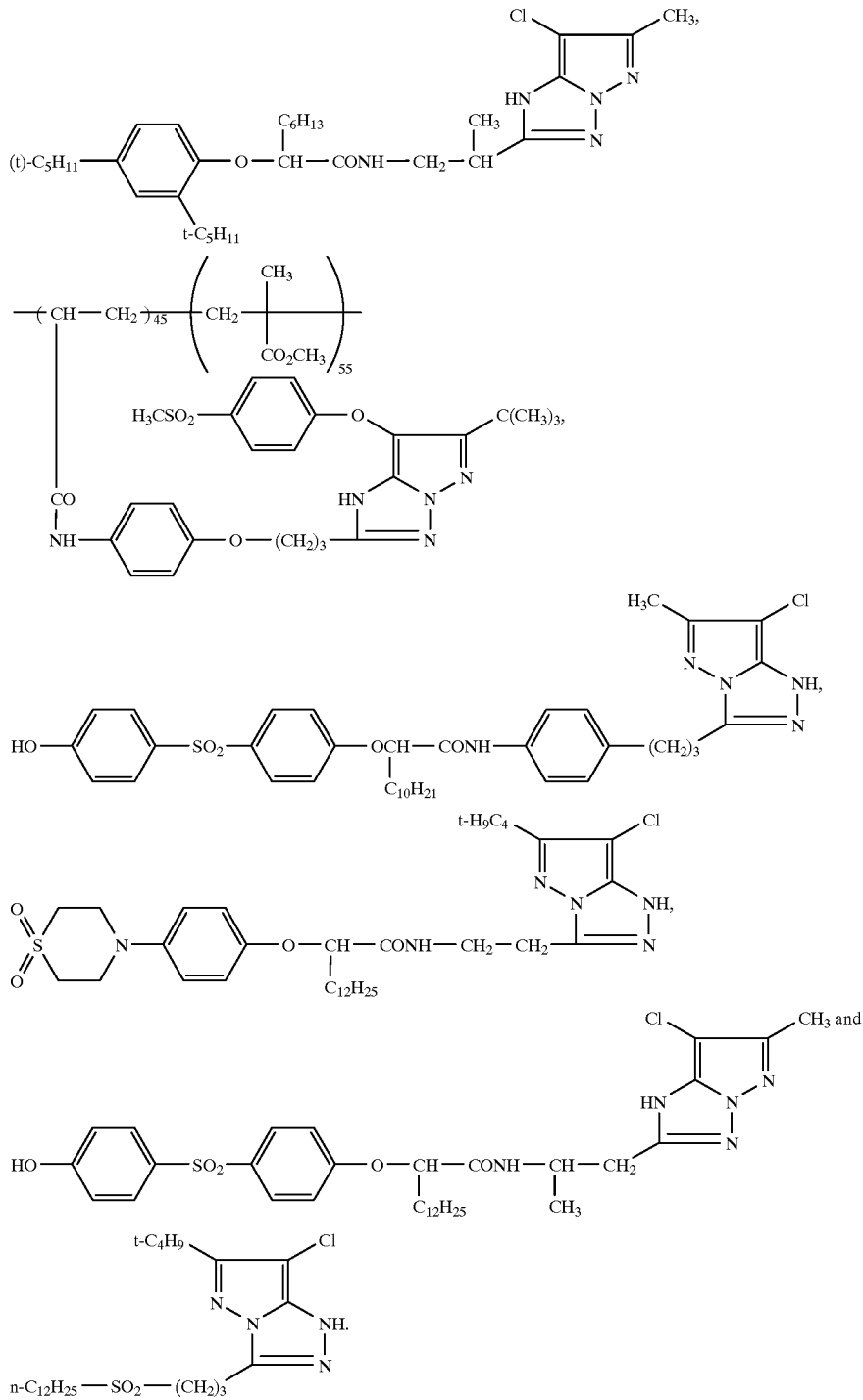

We claim:

1. A color photographic recording material which comprises on a support, at least one blue-sensitive silver halide emulsion layer with which a yellow coupler is associated, at least one green-sensitive silver halide emulsion layer with which a magenta coupler is associated, and at least one red-sensitive silver halide emulsion layer with which a cyan coupler is associated, light-insensitive intermediate layers between the layers of different color-sensitivity, wherein at least one of said magenta coupler in at least one green-sensitive silver halide emulsion layer is a pyrazolotriazole coupler and at least one of said layers contains a developer oxidation product ("DOP") scavenger, a compound of formula I

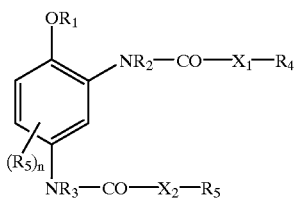

wherein
$X_1$ and $X_2$ are identical or different and are a single bond, —O— or —$NR_7$—,
$R_1$ is hydrogen or a group which can split off under the conditions of chromogenic development,
$R_2$ is hydrogen or —CO—$X_1$—$R_4$,
$R_3$ is hydrogen or —CO—$X_2$—$R_5$,
$R_4$ and $R_5$ are identical or different and are hydrogen, alkyl, alkenyl or a heterocyclic group,
$R_6$ is alkyl, aryl, acyl, alkoxy, aryloxy, acyloxy, halogen, —OH, —COOM, —$SO_3M$, —CN or —$NO_2$,
$R_7$ is hydrogen, alkyl, aryl or acyl,
M is hydrogen or a cation, and
n is 0, 1, 2 or 3 and wherein at least one $R_2$ or $R_3$ substituent is hydrogen.

2. The color photographic recording material according to claim 1, wherein
$X_1$ and $X_2$ are identical or different and are a single bond, —O— or —$NR_7$—,
$R_1$ is hydrogen,
$R_2$ is hydrogen or —CO—$X_1$—$R_4$,
$R_3$ is hydrogen or —CO—$X_2$—$R_5$,
$R_4$ and $R_5$ are identical or different and are represent alkyl or aryl,
$R_6$ is alkyl, acyl, alkoxy or chlorine,
$R_7$ is hydrogen, alkyl or aryl,
M is hydrogen or a cation, and
n is 0 or 1, and
in addition, at least one $R_2$ or $R_3$ substituent is hydrogen.

3. The color photographic recording material according to claim 1, wherein
$X_1$ and $X_2$ are identical or different and are a single bond, —O— or —$NR_7$—,
$R_1$, $R_2$ and $R_3$ are hydrogen,
$R_4$ and $R_5$ are identical or different and are alkyl or aryl,
$R_6$ is alkyl, acyl, alkoxy or chlorine,
$R_7$ is hydrogen, alkyl or aryl,
M is hydrogen or a cation,
n is O or 1.

4. The color photographic recording material according to claim 1, wherein the DOP scavenger of formula I is in at least one light-insensitive intermediate layer.

5. The color photographic recording material according to claim 1, wherein the compound of formula I used in an amount of 10 to 1000 mg/m² per layer in the material.

6. The color photographic recording material according to claim 1, wherein the pyrazolotriazole coupler is used in an amount of 50 to 800 mg/m² in the photographic material.

7. The color photographic material according to claim 1, wherein the compound of the formula I is selected from the group consisting of

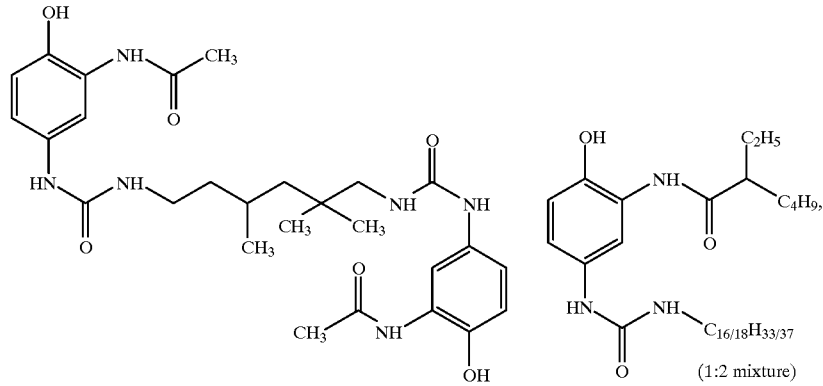

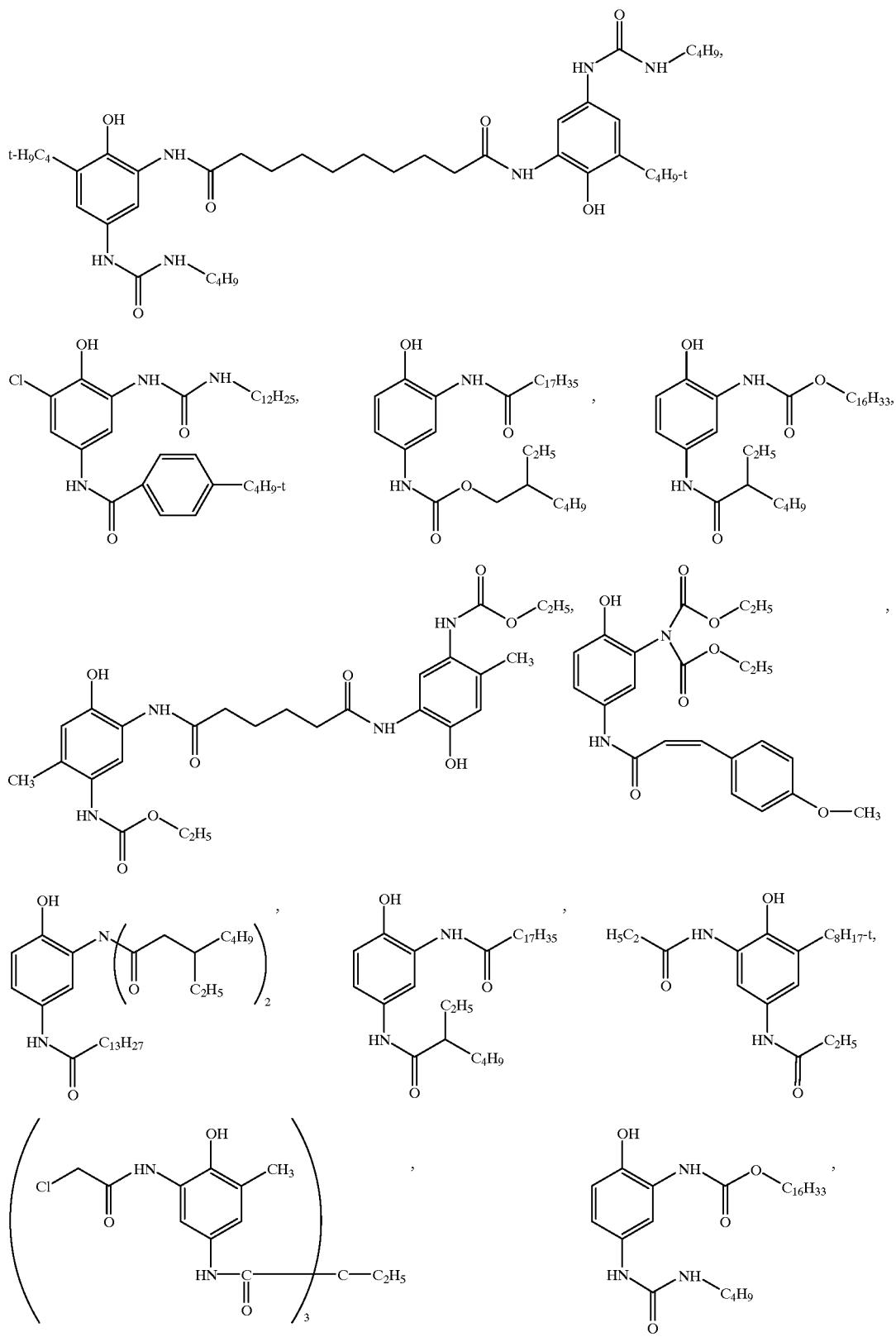

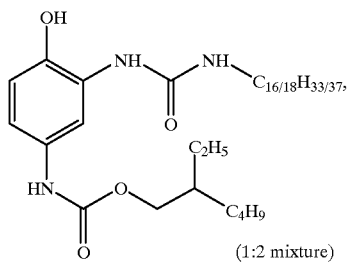
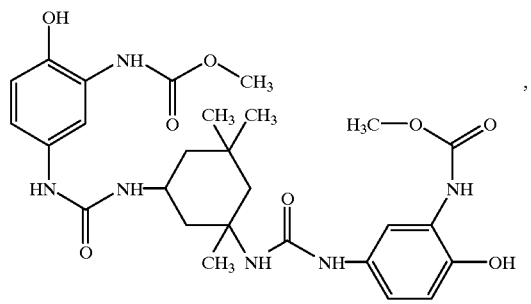
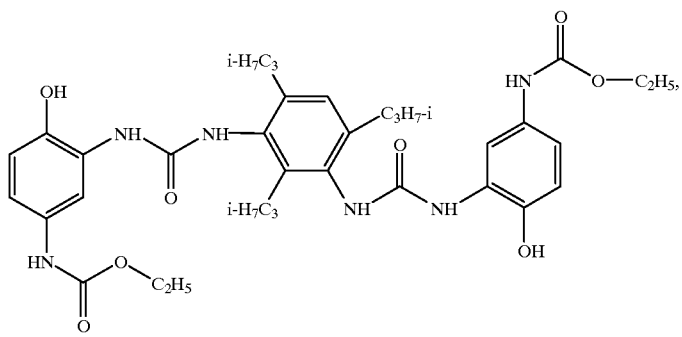
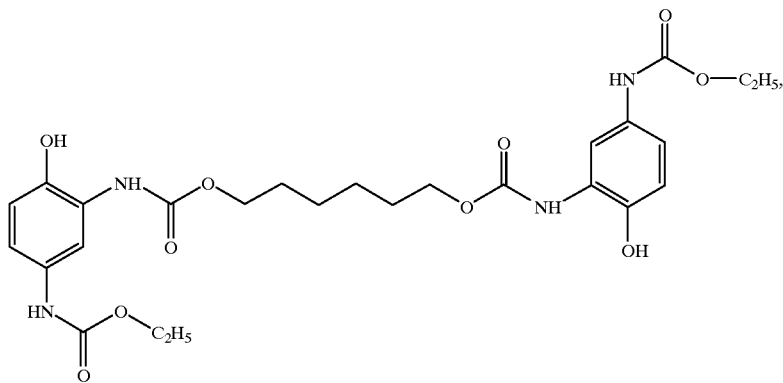
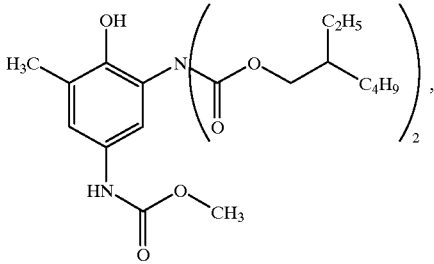
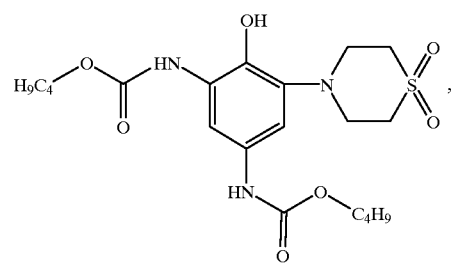
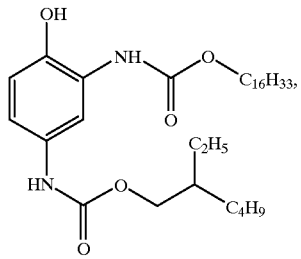
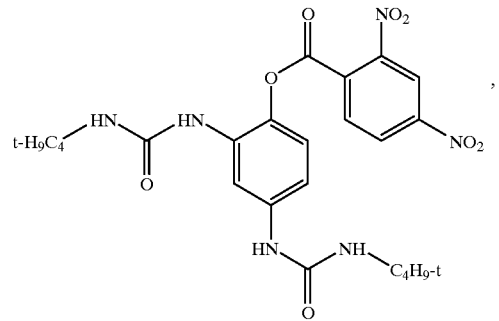

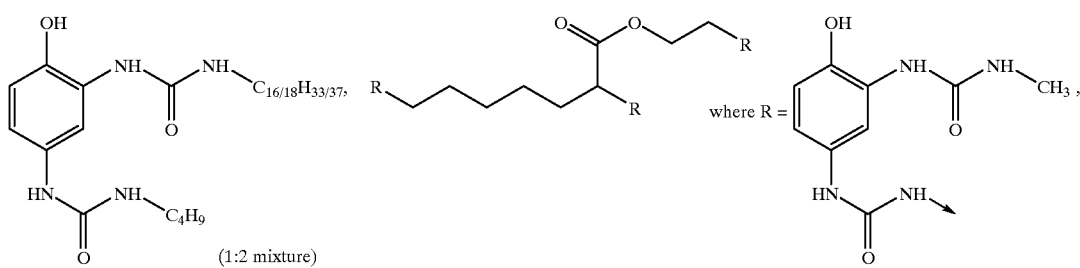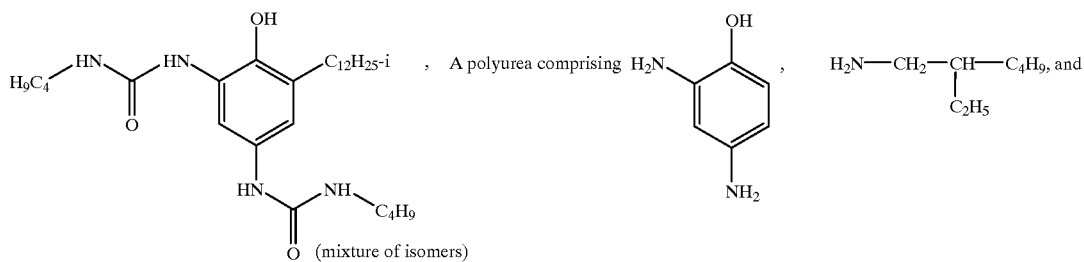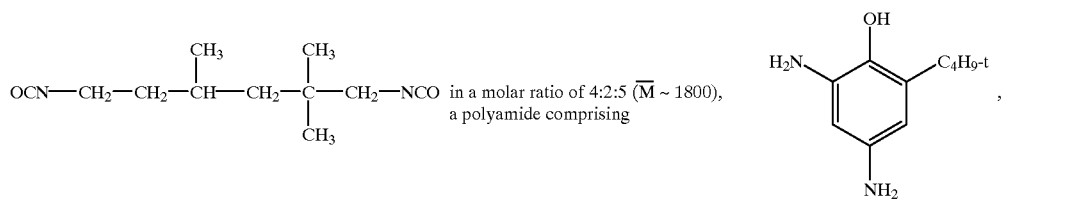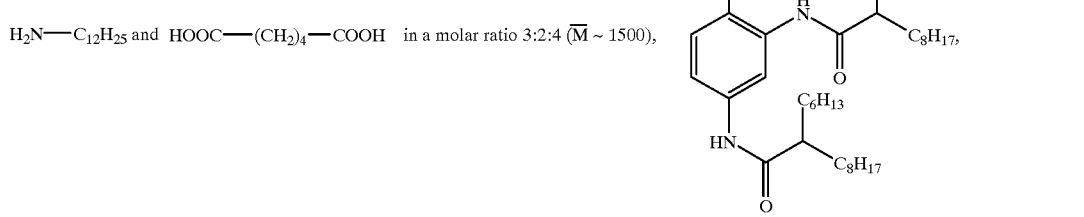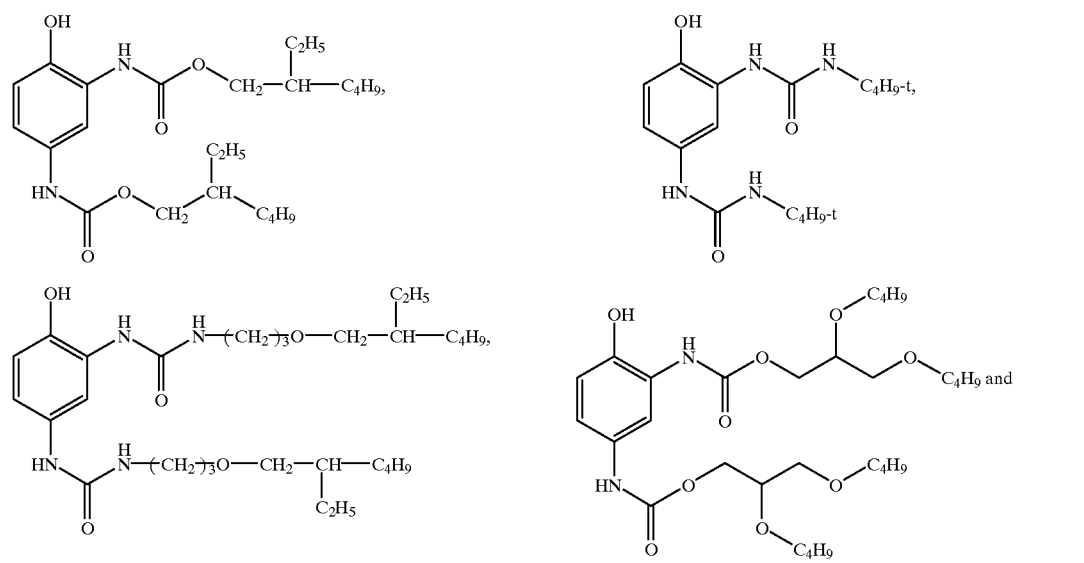

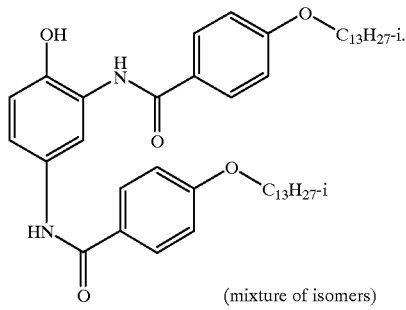

(mixture of isomers)

8. The color photographic recording material according to claim 1, wherein the pyrazolotriazole coupler corresponds to formula II

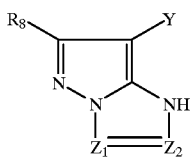
(II)

wherein $R_8$ represents hydrogen, halogen, alkyl, aryl, a heterocyclic group, cyano, alkoxy, acyloxy, carbamoyloxy, acylamino or a polymer residue, Y represents hydrogen or a group which can split off under the conditions of chromogenic development, one of the $Z_1$ and $Z_2$ radicals represents a nitrogen atom and the other represents —$CR_9$—, and $R_9$ has the same meaning as $R_8$, wherein one of the $R_8$ and $R_9$ radicals is a ballast group or is substituted by a ballast group, wherein the ballast group may also be a polymer residue.

9. The color photographic color material according to claim 8, wherein Y is hydrogen, chlorine, alkyl, aryl, acyl or

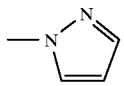

10. The color photographic recording material according to claim 8, wherein $R^8$ and $R^9$ together have at least 15 carbon atoms.

11. The color photographic recording material according to claim 8, wherein the coupler of formula II is selected from the group consisting of